US011851528B2

(12) United States Patent
Van Laarhoven et al.

(10) Patent No.: US 11,851,528 B2
(45) Date of Patent: Dec. 26, 2023

(54) PROCESS FOR PREPARING A POLYAMIDE, A NYLON SALT TO BE USED THEREIN AND A PROCESS FOR MAKING THE SALT

(71) Applicant: DSM IP ASSETS B.V., Heerlen (NL)

(72) Inventors: Bas Van Laarhoven, Echt (NL); Christiaan Johannes Cornelis Stoelwinder, Echt (NL); Mark Helmsing, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 19 days.

(21) Appl. No.: 17/513,665

(22) Filed: Oct. 28, 2021

(65) Prior Publication Data

US 2022/0098368 A1 Mar. 31, 2022

Related U.S. Application Data

(62) Division of application No. 16/778,822, filed on Jan. 31, 2020, now Pat. No. 11,299,589, which is a division of application No. 15/329,270, filed as application No. PCT/EP2015/073639 on Jul. 29, 2015, now Pat. No. 10,584,206.

(30) Foreign Application Priority Data

Jul. 29, 2014 (EP) .................................. 14178927

(51) Int. Cl.
| | |
|---|---|
| *C08G 69/30* | (2006.01) |
| *C08G 69/26* | (2006.01) |
| *C08G 69/28* | (2006.01) |
| *B01J 2/04* | (2006.01) |
| *C07C 51/41* | (2006.01) |
| *C07C 209/68* | (2006.01) |
| *C08J 3/12* | (2006.01) |

(52) U.S. Cl.
CPC ................ *C08G 69/30* (2013.01); *B01J 2/04* (2013.01); *C07C 51/412* (2013.01); *C07C 209/68* (2013.01); *C08G 69/26* (2013.01); *C08G 69/265* (2013.01); *C08G 69/28* (2013.01); *C08J 3/12* (2013.01); *C08J 2377/06* (2013.01)

(58) Field of Classification Search
CPC ............. C08G 69/30; C08G 69/26; C08J 3/12
See application file for complete search history.

(56) References Cited

U.S. PATENT DOCUMENTS

| | | | |
|---|---|---|---|
| 3,365,428 A | 1/1968 | Wujciak | |
| 4,603,193 A | 7/1986 | Richardson | |
| 4,627,940 A | 12/1986 | Beaver | |
| 9,850,348 B2 * | 12/2017 | Grolman | ................ C08G 69/30 |
| 2013/0172521 A1 | 7/2013 | Nakai | |
| 2015/0361216 A1 | 12/2015 | Grolman | |
| 2015/0368400 A1 | 12/2015 | Rulkens | |
| 2016/0060460 A1 | 3/2016 | Welch | |

FOREIGN PATENT DOCUMENTS

| | | |
|---|---|---|
| EP | 0 455 066 | 11/1991 |
| EP | 0 812 338 | 12/1997 |
| EP | 0 971 869 | 1/2000 |
| GB | 801733 | 9/1958 |
| WO | 2013/014236 | 1/2013 |

OTHER PUBLICATIONS

International Search Report for PCT/EP2015/073639 dated May 9, 2016, 5 pages.
Hemati et al, Fluidized bed coating and granulation: influence of process-related variables and physicochemical properties on the growth kinetics, Powder Technology 130 (2003), pp. 18-34, published on Jan. 2003.

* cited by examiner

*Primary Examiner* — Gregory Listvoyb
(74) *Attorney, Agent, or Firm* — NIXON & VANDERHYE P.C.

(57) ABSTRACT

Processes for preparing a polyamide, a polyamide material obtained by such processes, a nylon salt to be used therein, and processes for making the nylon salt are disclosed. The processes for preparing the polyamide include a direct solid state polymerization process. The salt used herein is a granulate material, prepared by a process, comprising spraying an aqueous solution comprising a diamine and a dicarboxylic acid dissolved in an aqueous medium, or an aqueous slurry comprising a diammonium dicarboxylate salt dispersed in an aqueous medium directly obtained from such an aqueous solution, onto or in a fluidized bed of diammonium dicarboxylate salt particles, while evaporating the aqueous medium, thereby forming a granulate salt material.

8 Claims, 4 Drawing Sheets

PROCESS FOR PREPARING A POLYAMIDE, A NYLON SALT TO BE USED THEREIN AND A PROCESS FOR MAKING THE SALT

CROSS-REFERENCE TO RELATED APPLICATIONS

This application is a divisional of commonly owned U.S. Ser. No. 16/778,822, filed Jan. 31, 2020 (now U.S. Pat. No. 11,299,589), which is a divisional of U.S. Ser. No. 15/329,270, filed Jan. 26, 2017 (now U.S. Pat. No. 10,584,206), which is the U.S. national phase of International Application No. PCT/EP2015/073639 filed Jul. 29, 2015 which designated the U.S. and claims priority to EP Patent Application No. 14178927.1 filed Jul. 29, 2014, the entire contents of each of which are hereby incorporated by reference.

FIELD

The present invention relates to a process for preparing a polyamide, a polyamide material obtainable by the said process, a nylon salt to be used therein, and a process for making the nylon salt.

BACKGROUND AND SUMMARY

A nylon salt is herein understood to be a diammonium dicarboxylate salt, also indicated as a diamine/dicarboxylic acid salt, in other words a salt prepared from a diamine or a mixture of diamines, and a dicarboxylic acid or a mixture of dicarboxylic acids. Polyamides prepared from such salts are generally indicated as AA-BB polyamides. Herein an AA-BB polyamide is understood to be a polyamide comprising alternating AA and BB repeating units, wherein AA represents the repeating units derived from diamine and BB represents the repeating units derived from dicarboxylic acid. Throughout this text the wordings "diammonium dicarboxylate salt" and "nylon salt" are meant to have the same meaning and are therefore interchangeable.

The process for preparing a polyamide of concern in the present invention is a direct solid state polymerization process. Such a process makes use of solid nylon salts, and throughout such process the salt and resulting polyamide and any intermediate prepolymer product thereof remain in the solid state. For the wording "direct solid state polymerization", also the abbreviation "DSSP" will be used herein.

In such a process, the salt used is typically in a powder or particular shape, and the aim is also to obtain the resulting polymer in a powder or particle shape. The salt used herein can be a salt powder or granulate, obtained for example, by spray drying, precipitation from solution, or a dry route process involving reaction of liquid diamine with solid dicarboxylic acid. The salt may also have a particular shape of compacted powder particles. Such a process is described, for example, in the patents U.S. Pat. No. 5,128,442 and GB-801,733.

In a DSSP process, the salt powder or granulate is heated to a reaction temperature below the melting temperature of the salt, thereby inducing polymerization of the salt and formation of the polyamide. While keeping the polymerization temperature below the melting point of the salt and the resulting polymer and its intermediates, the polymer is generally obtained, or at least intended to be obtained as a granulate material. Such a DSSP process is suitably carried out in a static bed reactor, or moving packed bed reactor. However, when carried out on large scale this can easily lead to agglomeration or caking of the powder or particulate material, thereby complicating the discharging of the polymer product from the reactor used. Another problem is linked to the heat transfer needed for heating the salt to the reaction temperature and for cooling the polymer before discharging. Because of the solid state and particulate form of the salt heat transfer is less efficient than in other processes wherein, for example, liquid melts or solutions are used. Limited heat transfer during polymerization can lead to an undesirable temperature profile throughout the reactor content, resulting in material varying in temperature history and consequently in a product with an inhomogeneous material composition. Heat transfer allowing for homogeneous heating is less a problem on small scale, i.e. on laboratory scale, but becomes more difficult at larger scales. Heating efficiency can be increased by using a process with a stirred reaction mass. Stirring may be accomplished in a reactor equipped with a mechanical agitator, such as a stirrer, or in tumbling reactor. A problem with direct solid state polymerization of solid nylon salts involving agitation and mixing of particulate material is that such a process, when applied on larger scale, still suffers from occurrence of agglomeration of particles, resulting in formation of much bigger particles or even lumps, or caking and scaling of the reactor, or suffers from extensive attrition of particles, resulting in fines, or even suffers from a combination of these problems. Fines create problems in further processing such as dusting, which creates an explosion risk, and limited flowability. Elimination of problems with dust in downstream processing would require additional measures for removing fines and dust. Lump formation can create problems in further processing, such as need for classification and grinding. Scaling on the wall can lead to reduced heat transfer and can thus complicate heating or cooling of the reactor content. This may lead to partially non-reacted material at spots at which heat transfer has been less efficient. Scaling on mechanical parts, such as on stirrers, can make stirring less efficient. With lump formation and scaling on valves, also discharging from the reactor can become more difficult. Scaling can also result in fouling of the reactor. It can result in residues in the reactor, which upon prolonged exposure to reaction conditions, such as elevated temperature, can lead to inhomogeneity in product properties, and to impurities, or even dark particles in the final product. To prevent build-up of scaling, leading to excessive scaling and further intensification of the above described associated problems, the reactor wall would have to be cleaned frequently, which will cause severe downtime of the plant.

An aim of the present invention is therefore to provide a process for preparing a polyamide wherein the above problems of agglomeration, fines and scaling are reduced at least in part or eventually fully absent. Another aim is to provide a nylon salt, that can be used in the said process, wherein the above problems are reduced at least in part or eventually fully absent. A further aim is to provide a nylon salt that reduces or eventually fully eliminates above problems, when used in a direct solid state polymerization process. A further aim is to provide a polyamide material that can be produced in an efficient manner, is easy to handle and requires less extensive and time consuming steps for cleaning and de-dusting.

These aims have been achieved with the following aspects of the present invention.

The first aspect concerns a process for preparing a nylon salt, which according to the present invention is prepared by fluidized bed spray granulation.

The second aspect of the invention concerns a nylon salt, wherein the salt is obtained by preparation in a fluidized bed spray granulation process.

The third aspect concerns a process for preparing a polyamide comprising direct solid state polymerization of a nylon salt, wherein the salt is a granulate salt material prepared by fluidized bed spray granulation.

A further aspect concerns a polyamide granulate material, comprising an AA-BB polyamide obtained by direct solid state polymerization of a diammonium dicarboxylate salt, the salt used being a salt prepared by fluidized bed spray granulation process.

The effect of the first and second aspect of the invention, being a fluidized bed spray granulation process and nylon salt obtained by said process, is that the salt is a granulate salt material that can be used in a direct solid state polymerization process while showing less problems in a direct solid state polymerization (DSSP) process compared to nylon salts in the form of granular or granulate material with particles of similar size and the same composition prepared via other routes. Discharging of the polymer produced by DSSP from the reactor has shown to be easier. Fouling of the reactor is reduced, while at the same time, agglomeration and formation of fines is limited. Reduced agglomeration and formation of fines is also demonstrated with analytical data on particle size distribution, showing that the particle size distributions of starting salt material and final polymer powder differ less when compared with those of polyamide granulate material obtained by DSSP from nylon salts of the same composition prepared via other routes. Furthermore, the polyamide material prepared by DSSP from the salt obtained by fluidized bed spray granulation, is produced in an efficient manner since it requires less extensive steps for cleaning and de-dusting, and is easy to handle.

BRIEF DESCRIPTION OF THE DRAWINGS

FIG. 1(a) is a microscopic photograph of the salt particles with a relative small average particle size and FIG. 1(b) is a photograph of the salt particles under further enlargement;

DETAILED DESCRIPTION

Figure 1A:
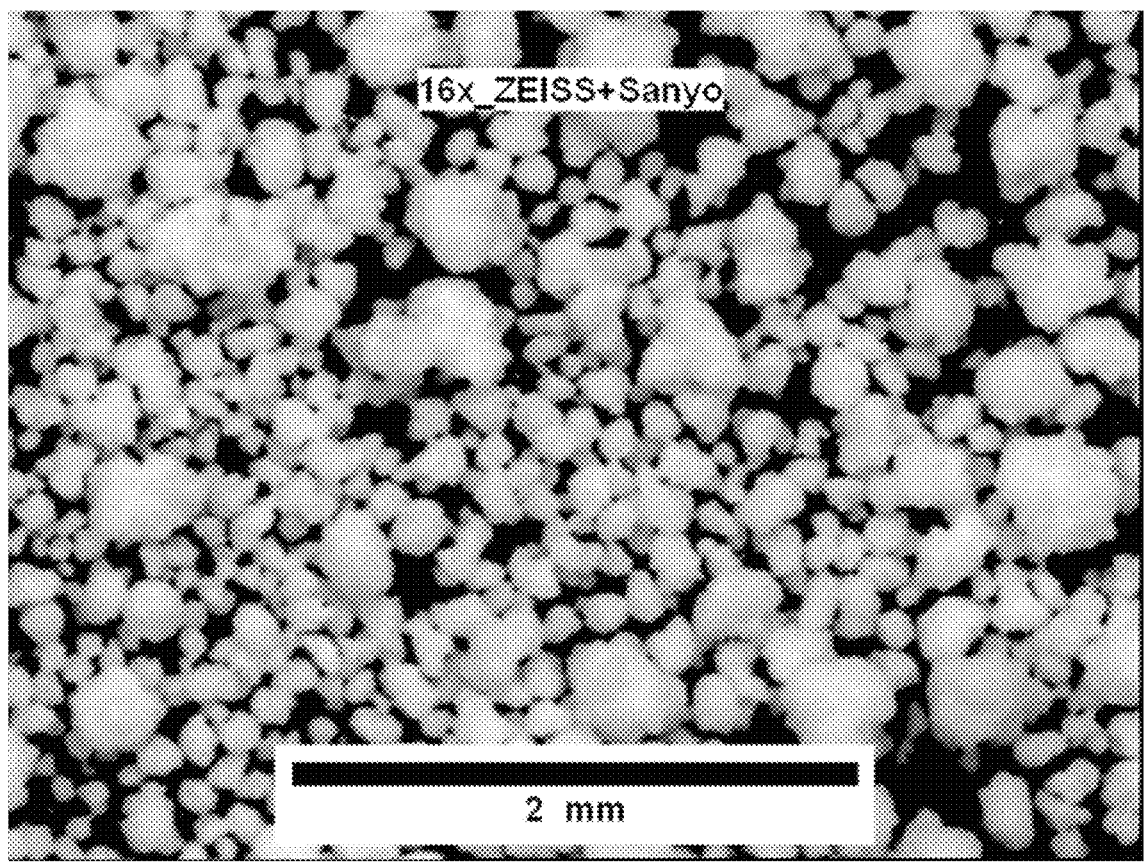
FIGS. 1(a) and 1(b) are photographs of a salt according to the invention wherein the salt particles tend to have a blackberry like structure, whereby

The process according to the invention for preparing the nylon salt, i.e. the diammonium dicarboxylate salt, is a fluidized bed spray granulation process. The process comprises spraying of an aqueous solution comprising a diamine, or a mixture of diamines, and a dicarboxylic acid or a mixture of dicarboxylic acids dissolved in an aqueous medium, or spraying an aqueous slurry comprising a diammonium dicarboxylate salt dispersed in an aqueous medium directly obtained from an aqueous solution comprising a diamine and a dicarboxylic acid dissolved in an aqueous medium, onto or in a fluidized bed of diammonium dicarboxylate salt particles, wherein a preheated gaseous medium is led through the fluidized bed, while evaporating the aqueous medium, thereby forming a granulate salt material.

It is noted that the diamine used in the process for preparing the nylon salt can be a single diamine, or a mixture of different diamines. Unless specifically noted otherwise, the single form diamine has the meaning of including both a single diamine and a mixture of different diamines. Analogously, the dicarboxylic acid used in the process for preparing the nylon salt can be a single dicarboxylic acid, or a mixture of different dicarboxylic acids. Unless specifically noted otherwise, the single form dicarboxylic acid has the meaning of including both a single dicarboxylic acid and a mixture of different dicarboxylic acid.

The expression "in the range of X-Y", wherein X and Y represent lower and upper limits, has the meaning that the range is from X up to and including Y. In other words, in said expression the values of both limits are included in the range.

With a granular or granulate material is herein understood a material consisting for at least 50 wt. % of particles with a particle size of at most 3 mm (millimeter). Such a material has a d50 of 3 mm or less. Herein the amount of particles with a particle size of at most 3 mm is determined by sieving and weighing. The particle size for the d50 value, respectively the wt. % of particles with a particle size of at most 3 mm is determined by the method according to DIN 66-165 part 1 and 2.

The slurry that can be used in the inventive salt preparation process is suitably directly obtained from an aqueous solution comprising a diamine and a dicarboxylic acid. This means that first the diamine and the dicarboxylic acid have to be completely dissolved in the aqueous medium, for example at elevated temperature, and then the slurry is formed, for example by cooling the solution. By cooling, first the saturation level for the dissolved salt will be reached and upon further cooling going beyond the saturation level, crystallization of the salt will occur. The advantage of preparing the slurry in this manner is that in the process for preparing the polyamide by DSSP, the amount of residual unreacted dicarboxylic acid, if any, is lower.

The aqueous medium comprised by the slurry or solution used in the inventive process comprises at least water. It may suitably comprise a co-solvent, such as an organic solvent. Preferably the co-solvent is a liquid that is miscible with water. Suitably the liquid miscible with water is an alcohol. Examples thereof include methanol and ethanol. Such liquids miscible with water may be used for example to increase the solubility of the salt in water. This can be advantageous for example with less hydrophilic components, such as longer chain diamines. The liquid miscible with water may also be used otherwise, for example to partially precipitate the salt from an aqueous solution, thereby forming a slurry. Suitably, the co-solvent is present in an amount of 0-50 wt. %, and more particular 0-25 wt. %, relative to the total weight of water and co-solvent. In a preferred embodiment, the aqueous medium consists of water. This has the advantage that no special precautions have to be taken for removal, separation or recycling of any co-solvent.

The aqueous solution or aqueous slurry used in the process according to the invention can have a salt concentration varying over a wide range, for example in the range from 2.5-80 wt. %. The concentration may well be in the range of 1-2.5 wt. %, or even below 1 wt. %. However, such low concentration would make the process less efficient in terms of energy consumption involved in the evaporation of the water. Suitably, the solution or slurry has a salt concentration of at least 5 wt. %, in particular at least 10 wt. %. Preferably, the salt concentration is in the range of 20-80 wt. %, still more preferably 25-70 wt. %. Herein the salt concentration is calculated as the weight percentage (wt. %) of total amount of diamine and dicarboxylic acid, relative to the total weight of the solution or slurry. For clarity: where in the process a mixture of diamines and/or a mixture of dicarboxylic acid is, for the calculation of the total amount of diamine and dicarboxylic acid, all the diamines in the mixture and all the dicarboxylic acids in the mixture have to be included. The maximum concentration will in practice be limited by the solubility of the salt. A higher minimum salt concentration has the advantage that less water has to be evaporated The aqueous solution or aqueous slurry may have a temperature varying over a wide range. When solubility allows, the temperature of the aqueous solution or aqueous slurry may well be about room temperature, i.e. about 20° C. or even lower. The temperature may be as high as the boiling point of water at atmospheric pressure, more particular 100° C., or even above 100° C., when the solution is pressurized. When a pressurized solution is used, spraying onto the fluidized powder bed results in partial evaporation of water upon release of the pressure, while removal of the remaining of the water will take place in the bed upon drying of droplets precipitated on other particles. For the pressurized conditions, suitably a temperature of at most 150° C. and a water content of at least 25 wt. %, relative to the total weight of the solution are applied.

Preferably said solution or slurry temperature is at least 35° C. and at most 100° C., and more preferably in the range of 40-95° C. An advantage of a higher solution or slurry temperature is that a higher salt concentration can be applied, making the drying in the process more efficient, and allowing for use of gas with a lower temperature. Use of a temperature below 100° C. avoids the need for a pressure reactor and a pressurized solution.

The solution or slurry may comprise, next to the nylon salt, respectively the constituting diamine and dicarboxylic acid, one or more other components. In principle any component can be present, as long as such component does not prohibit the formation of solid salt particles in the fluidized bed spray granulation process and the polymerization of the nylon salt in a DSSP process. Suitably, such other components, if present at all, are selected from components that are useful during the polymerization, or are useful in the polyamide composition to be prepared. Preferably, the solution or slurry comprises at least one component selected from polymerization catalysts, stabilizers and inert fillers. If used at all, the amount of other components is preferably limited.

The aqueous solution or slurry suitably consists of
a) 20-90 wt. % of the aqueous medium;
b) 10-80 wt. % of salt, either dissolved or dispersed in the aqueous medium; and
c) 0-25 wt. % of other components;
wherein the weight percentages (wt. %) are relative to the total weight of the aqueous solution or slurry, and wherein the sum of a), b) and c) amounts to 100 wt. %.

Preferably, the aqueous solution or slurry consists of
a) 20-90 wt. % of the aqueous medium;
b) 10-80 wt. % of salt, either dissolved or dispersed in the aqueous medium;
c) 0-2.5 wt. % of at least one polymerization catalyst and/or at least one stabilizers; and
d) 0-22.5 wt. % of other components;
wherein the weight percentages (wt. %) are relative to the total weight of the aqueous solution or slurry, and wherein the sum of a), b), c) and d) amounts to 100 wt. %.

The preparation of granulate salt material by fluidized bed spray granulation is supposed to proceed as follows: a salt solution or salt slurry is sprayed onto a fluidized bed of particles. Droplets formed by the spraying can form a liquid bridge between two or more particles, thereby forming small agglomerates. Other droplets formed by the spraying may dry to form new small particles. These new small particles may be bridged together to form new small agglomerates or may be incorporated into other agglomerates, thereby growing these agglomerates, and ultimately resulting in larger agglomerates. Meanwhile, the solvent in the liquid bridges will evaporate thereby solidifying the smaller and larger agglomerates. The larger agglomerates may reach a certain size at which the particles become more difficult to fluidize. Such larger particles might be allowed to settle or be removed from the fluidized bed. The remaining smaller agglomerates in the fluidized bed will grow to larger agglomerates, while in the meantime new small agglomerates will have formed and thus allow the process to be continued. The larger agglomerates thus formed typically have a kind of blackberry structure. When growing even larger, the agglomerates may become more rounded off, but can still show remaining images of the smaller particles bound together in the larger agglomerates. Additionally a different way of growing larger particles may occur, namely by deposition of multiple droplets of the solution or slurry on the surface of a particle, which deposited droplets spread and dry, thereby leading to a kind of onion like structure, at least so at the surface layers. Thus, the granulate salt material obtained by the process according to the invention suitably comprises particles having an agglomerated shape or an onion like shape.

Suitably, the process is started with preparing a fluidized bed of precursor particles. For the precursor particles, in principle any particulate material that can be fluidized can be used. For instance, if the process is carried out as a semi-continuous process, the salt with the precursor particles produced in the initial stage may be removed. In case of a batch wise production, where removal is not that easy, the precursor particles are suitably selected from materials that may be comprised by the polyamide composition ultimately being produced.

Preferably, the precursor particles consist of nylon salt. The advantage is that such precursor salt can be copolymerized with the nylon salt obtained from the salt solution. More preferably the precursor salt particles have the same composition as the nylon salt obtained from the salt solution.

Suitably, the precursor particles are salt particles obtained by spray drying. Once granulate salt material obtained from the inventive process of fluidized bed spray granulation is available, also such granulate salt material may be used as precursor particles for preparing the fluidized bed at the start or restart of the process.

A fluidized bed can be created starting from a precursor material in particle form, and using a gaseous medium for fluidization of the precursor particles. The gaseous medium is also used for drying of the solution or slurry sprayed in or onto the fluidized bed.

The gaseous medium led through the fluidized bed is suitably preheated. This contributes to a more effective drying of the sprayed solution or slurry. It preferably has a temperature of at least 50° C., more particular at least 70° C. This has the advantage that the water evaporates faster and drying is more efficient. Herein the temperature of the gaseous medium is measured before entering into the fluidized bed. More preferably, the temperature is in the range of 80-250° C., in particular in the range of 100-200° C. Too high of a temperature for the gaseous medium may lead to degradation of one of its constituents and/or coloration of the salt product or, and eventually may turn the product yellow. A lower maximum temperature has the advantage that a salt with less to none coloration is obtained.

For aliphatic salts the maximum gas temperature is preferably even lower, e.g. below 175° C., more particular below 150° C. This reduces the risk of sticking of the salt particles formed on hot parts in the equipment. Aliphatic salts generally have a lower melting point than their semi-aromatic counterparts.

Aliphatic salt are herein understood diammonium dicarboxylate salts consisting of aliphatic diamine and aliphatic dicarboxylic acid.

Semi-aromatic salt are herein understood diammonium dicarboxylate salts comprising at least an aromatic constituent and at least an aliphatic constituent. Suitably, the semi-aromatic salt consists of aromatic diamine and aliphatic dicarboxylic acid, or consisting of aliphatic diamine and aromatic dicarboxylic acid, or consisting of diamine and dicarboxylic acid, wherein at least one of the diamine and the dicarboxylic acid is partially aromatic and partially aliphatic. The diamine is herein considered to be partially aromatic and partially aliphatic, when it consists of at least two diamines, comprising at least one aromatic diamine and at least one aliphatic diamine. The dicarboxylic acid is herein considered to be partially aromatic and partially aliphatic, when it consists of at least two dicarboxylic acids, comprising at least one aromatic dicarboxylic acid and at least one aliphatic dicarboxylic acid.

The diamine can also be fully aliphatic and comprising at least two different aliphatic diamines. The dicarboxylic acid can also be fully aromatic and comprising at least two different aromatic dicarboxylic acids.

The salt may also be fully aromatic, i.e. consisting of an aromatic dicarboxylic acid and an aromatic diamine. Example of suitable aromatic salts are MXDT and PXDT. Such a salt can be dissolved or prepared from its constituent diamines meta-xylenediamine (MXD) respectively para-xylenediamine (PXD) and terephthalic acid (T) as carboxylic acid, in water or in an aqueous liquid, can be isolated from an aqueous solution by fluidized bed spray granulation, and can also be polymerized by direct solid state polymerization.

After the gaseous medium has passed through the fluidized bed, it can be removed as off-gas. The off-gas can be exhausted or recycled, or a combination thereof such that a part is exhausted and another part is recycled. When being recycled, it may also be used to be fed back into the spray granulation process. Suitably, off-gas resulting from the gaseous medium led through the fluidized bed, is passed through a filter or through a scrubber, or is dried, or any combination thereof, before being exhausted or recycled.

For the gaseous medium, any gas suitable for fluidization and drying may be used. Preferably, the gaseous medium is an inert gas, preferably nitrogen. Air or oxygen in combination with very fine particles constitutes an explosion risk. Use of inert gas has the advantage of a reduced explosion risk.

The temperature of the fluidized bed can be varied over a wide range, as long as the temperature remains below the melting temperature of the nylon salt. The fluidized bed suitably has a temperature of at least 35° C., whereas for low melting salts an even lower temperature may be applied. Suitably, the bed temperature is also at least 50° C. below the melting point of the salt.

The terms melting point and melting temperature are herein understood to have the same meaning, and therefore interchangeable. With the melting point, or melting temperature of the salt is herein understood the temperature, measured by the DSC method according to ISO-11357-1/3, 2011, on pre-dried samples in an N2 atmosphere with heating and cooling rate of 10° C./min. Herein Tm has been calculated from the peak value of the highest melting peak in the first heating cycle. Herein the granulate salt material is dried during 24 hours at 105° C. and under a vacuum of 100 mmHg.

Herein the bed temperature is measured in the center of the bed. Preferably, said bed temperature is in the range of 40-100° C., in particular in the range of 50-80° C. A higher bed temperature has the advantage that the salt in the bed will dry faster and better and the particulate salt material produced will have a lower residual moisture content. A lower maximum temperature is favorably applied for lower melting salts, such as for aliphatic salts or semi-aromatic salts comprising aliphatic dicarboxylic acid.

Suitably, the fluidized bed has a temperature of at least 35° C., while the aqueous solution or aqueous slurry has a temperature of at least 35° C. and the gaseous medium led through the fluidized bed has a temperature of at least 50° C.

The temperature of the fluidized bed can be steered, for example by selecting a concentration, a temperature and a spraying speed for the solution or slurry and adjusting the temperature and throughput of the gaseous medium.

Suitably, the granulate salt material has a residual moisture content of at most 7.5 wt. % or better at most 5 wt. %, preferably at most 4 wt. %, more preferably at most 2 wt. %, still more preferably at most 1 wt. %. Herein the weight percentage (wt. %) is relative to the total weight of the granulate salt material including the residual moisture. The advantage of a lower water content is reduced risk of caking upon storage. With moisture is herein understood water, and where applicable any co-solvent, retained in the granulate salt material obtained after the fluidized bed spray granulation process. The residual moisture content is measured by determining the weight loss of the granulate salt material upon drying of the salt during 24 hours at 105° C. and under a vacuum of 100 mmHg. The residual moisture content is calculated from the weight loss expressed as weight percentage relative to the weight of the granulate salt material before drying.

The residual water content of the granulate salt material as obtained from the fluidized bed spray granulation can be further reduced afterwards. The residual water content may be reduced, for example, by drying the granulate salt material in a fluidized bed. For the drying in a fluidized bed, conventional fluid bed units and fluid bed technology for drying of particles—powders, agglomerates or pellets—can be used. Herein, for example, process air is supplied through a special perforated distributor plate and flows through the bed of solids at a velocity sufficient to support the weight of particles in a fluidized state.

The particle size of the granulate salt material is the result of a balance between several process parameters. Increasing the residence time of the particles in the granulator (e.g. by increasing the volume of the fluidized bed and/or decreasing the outflow of the granulate) will generally result in coarser particles. Suitably, in the fluidized bed spray granulation process, a classification leg or classification channel with classification air is used. Herein, the classification air can be adjusted in such a way, that particles with the required particle size can leave the reactor and smaller particles stay in the fluidized bed. Therefore, a higher gas flow rate in the classification leg will lead to larger particles.

Suitably, the granulate salt material has a particle size distribution with a median particle size (d50) in the range of 100-3000 µm, more particular in the range of 150-2000 µm. Preferably the d50 is in the range of 200-1000 µm, more preferably 250-750 µm. Herein the particle size distribution is measured with laser granulometry by the method according to ISO 13320-1 at 20° C. The advantage of having a particle size in the preferred range is that it combines good flowability with good polymerization characteristics.

The process according to the invention may be carried out in conventional apparatus for fluidized bed spray granulation. The process may be carried out, for example, in a vertical set-up comprising a substantially round fluidized bed apparatus with a classification channel, or in an essentially horizontal set-up comprising a flow channel, and applying a horizontally moving bed as a plug flow. During or after the fluidized bed spray granulation, the material located in the fluidized bed or discharged therefrom may be subjected to a conventional classification process. In the horizontal set-up the particle size is controlled by adjusting the dosing rate versus the speed of the plug flow.

Fines separated in a classification step may be reused, for example, as precursor particles for preparing a fluidized bed at the start of the process. The start of the process may be start of a new batch in a vertical set-up, or the initial part of a horizontally moving bed in an essentially horizontal set-up.

Preferably, the process is carried out in a vertical set-up comprising a substantially round fluidized bed apparatus with a classification channel. The advantage thereof is that control of the particle size is done in one go by adjusting the speed of the gas flow in the classification channel in the vertical set-up, meanwhile resulting in a narrow particle size distribution without the need for a separate step for the separation of fines.

In the process according to the invention, in principle any nylon salt can be prepared provided that the salt, or the constituent components thereof, can be dissolved in an aqueous medium and an aqueous solution of the constituting diamine(s) and the dicarboxylic acid(s) can be prepared. Forming of a granulate salt material is generally no issue since dry or substantially dry nylon salts are typically solid materials at room temperature.

The salt suitably is a salt of a single diamine and a single dicarboxylic acid. The salt may also be a mixed salt, made from multiple components. The mixed salt is suitably made of components comprising at least two diamines and one dicarboxylic acid, or one diamine and at least two dicarboxylic acids, or even at least two diamines and at least two dicarboxylic acids.

Suitable, the diamine used for the salt in the process according to the invention is selected from aliphatic diamines, or aromatic diamines, or any combination thereof. Examples of suitable aliphatic diamines are ethylene diamine, 1,3-propane-diamine, 1,4-diaminobutane, 1,5-pentanediamine, 2-methyl-1,5-pentanediamine, 1,6-hexanediamine, 2,2,4-trimethyl-1,6-hexanediamine, 2,4,4-trimethyl-1,6-hexanediamine, cis-1,4-cyclohexanediamine, trans-1,4-cyclohexanediamine, isophorone diamine, 1,7-heptanediamine, 1,8-octanediamine, 1,9-nonanediamine, 1,10-decanediamine, 1,11-undecanediamine, 1,12-dodecanediamine, 1,13-tridecanediamine, 1,14-tetradecanediamine, 1,15-pentadecanediamine, 1,16-hexadecanediamine, 1,17-heptadecanediamine, 1,18-octadecanediamine, 1,19-nonadecanediamine, and 1,20-eicosanediamine. Examples of suitable aromatic diamines are 1,4-diaminobenzene, 1,3-diaminobenzene, 1,4-naphthalenediamine, 1,5-naphthalenediamine 2,6-naphthalenediamine, meta-xylenediamine and para-xylenediamine.

Preferably, the diamine comprises at least an aliphatic C2-C10 diamine, i.e. an aliphatic diamine with from 2 up to and including 10 carbon atoms. The advantage thereof is that the salt resulting from the diamine has a higher solubility in water. More preferably, the diamine comprises one or more than one aliphatic C2-C10 diamine in an amount of at least 50 mole %, relative to the total molar amount of diamine. Still more preferably, the amount of aliphatic C2-C10 diamine is at least 75 mole %, relative to the total molar amount of diamine.

In a particular embodiment, the diamine comprises one or more than one aliphatic C4-C6 diamine in an amount of at least 50 mole %, relative to the total molar amount of diamine. More particular, the amount of aliphatic C4-C6 diamine is at least 75 mole %, relative to the total molar amount of diamine. The aliphatic C4-C6 diamine suitably consists of a diamine selected from 1,4-diaminobutane, 1,5-pentanediamine, 2-methyl-1,5-pentanediamine and 1,6-hexanediamine, or any mixture thereof; preferably selected from 1,4-diaminobutane, 1,5-pentanediamine and 1,6-hexanediamine, or any mixture thereof.

Suitably, the dicarboxylic acid is selected from aromatic dicarboxylic acid, or aliphatic dicarboxylic acid, or any combination thereof.

Suitable examples of aromatic dicarboxylic acids are terephthalic acid, isophthalic acid, 2,6-naphthalene dicarboxylic acid, 4,4'-diphenyl dicarboxylic acid.

For the aliphatic dicarboxylic acids suitable examples are oxalic acid, succinic acid, 1,5-pentanedicarboxylic acid, adipic acid, 1,7-heptanedioic acid, 1,8-octanedioic acid, azaleic acid, sebacic acid, 1,11-undecanedioic acid, 1,12-dodecanedioic acid, 1,13-tridecanedioic acid, 1,14-tetradecanedioic acid, 1,15-pentadecanedioic acid, 1,16-hexadecanedioic acid, 1,17-heptadecanedioic acid, 1,18-octadecanedioic acid, 1,19-nonadecanedioic acid, and 1,20-eicosanedioic acid.

Preferably, the dicarboxylic acid comprises a C4-C10 aliphatic dicarboxylic acid, i.e. an aliphatic dicarboxylic acid with from to 4 up to and including 10 carbon atoms. The advantage thereof is that the salt resulting from the dicarboxylic acid has a higher solubility in water, allowing the use of a higher salt concentration and less water to be evaporated. More preferably, the dicarboxylic acid comprises adipic acid.

Also preferably, the dicarboxylic acid comprises an aromatic dicarboxylic acid. The advantage of this selection is that the temperature conditions applied in the fluidized bed spray granulation can be varied over a wider range. For example, due to the higher melting point of salts comprising an aromatic dicarboxylic acid the temperature of the heated air applied for drying may be higher. Examples of salts that can be prepared with the process according to the invention include the following semi-aromatic salts: XT, XI, XT/XI, XT/X6, XT/Y6 and XT/YT, and any combinations thereof, wherein T represents terephthalic acid, I represents isophthalic acid, 6 represents adipic acid, and X and Y represent diamines.

In a preferred embodiment X and Y are different diamines independently from each other chosen from aliphatic diamines from the group consisting of ethylene diamine, 1,4-diaminobutane, 1,5-pentanediamine, 2-methyl-1,5-pentanediamine, 1,6-hexanediamine, 2,2,4-trimethyl-1,6-hexanediamine, 2,4,4-trimethyl-1,6-hexanediamine, cis-1,4-cyclohexanediamine, trans-1,4-cyclohexanediamine, 1,8-octanediamine, 1,9-nonanediamine, and 1,10-decanediamine.

Other examples of salts that can be prepared with the process according to the invention include the following aliphatic salts: 46, 66, 46/66, 66/68, and 410, and any combinations thereof.

The salts may also be mixed salts, for example comprising a mixture of components from any of the mentioned semi-aromatic salts XT, XI, XT/XI, XT/X6, XT/Y6 and XT/YT and any of the aliphatic salts 46, 66, 46/66, 66/68, and 410.

In a particular embodiment of the process according to the invention the diamine comprises an aromatic diamine and/or an aliphatic C2-C10 diamine and the dicarboxylic acid comprises a C4-C10 aliphatic dicarboxylic acid and/or an aromatic dicarboxylic acid.

In a preferred embodiment of the invention, the dicarboxylic acid in the salt comprises terephthalic acid, for example in an amount of at least 50 mole %, more particular at least 75 mole %, or even consists of terephthalic acid. The mole % is herein calculated as mole %, relative to the total molar amount of dicarboxylic acid. The advantage is that in case of occurrence of residual terephthalic remaining in the polyamide produced upon direct solid state polymerization, such residual acid can be reduced more effectively by post dosing of diamine, than for similar salts prepared via a dry route.

In a more preferred embodiment, the dicarboxylic acid consists for at least 75 mole % of terephthalic acid, and the diamine consists for at least 75 mole % of 1,6-hexamethylediamine (HMDA) and/or 1,4-diaminobutane (DAB) and/or 1,5-pentanediamine.

Preferably the diamine comprises 1,6-hexamethylediamine (HMDA) and 1,4-diaminobutane (DAB) in a molar ratio DAB/HMDA in the range of 25:7-45:55, or even better 30:70-40:60, as this gives rise to a polyamide with eutectic melting point.

Also preferable, the diamine comprises 1,6-hexamethylediamine (HMDA) and 1,5-pentanediamine (PD) in a molar ratio PD/HMDA in the range of 30:70-70:30, or even better 40:60 40:60-60:40.

Even more preferred the dicarboxylic acid consists for 95-100 mole % of terephthalic acid, and the diamine consists for at least 95-100 mole % of 1,6-hexamethylediamine (HMDA), 1,4-diaminobutane (DAB) or 1,5-pentanediamine. Suitably, the corresponding polyamides are either homopolymers PA-4T, PA-5T or PA-6T, or copolymers thereof such as PA4T/5T, PA-4T/6T and PA-5T/6T, or PA-4T/5T/6T.

In the process according to the invention, the dicarboxylic acid and the diamine do not need to be present in exact equimolar amounts. Excess of dicarboxylic acid may be compensated by dosing extra diamine during polymerization. Excess of diamine is generally already lost during fluidized bed spray granulation and otherwise may result in diamine loss during polymerization but such salts can still be polymerized to high molecular weight polyamides. Preferably, the dicarboxylic acid and the diamine are present in a molar ratio in the range of 0.95:1-1.05:1, preferably 0.98:1-1.02:1, more preferably 0.99:1-1.01:1.

The invention also relates to a nylon salt. The nylon salt according to the invention is a granulate salt material comprising a diammonium dicarboxylate (salt obtainable by fluidized bed spray granulation. The nylon salt according to the invention has the advantages in a DSSP process, as mentioned above.

Figure 1B:
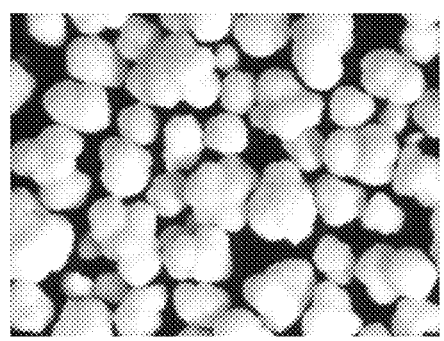
Figure 2:
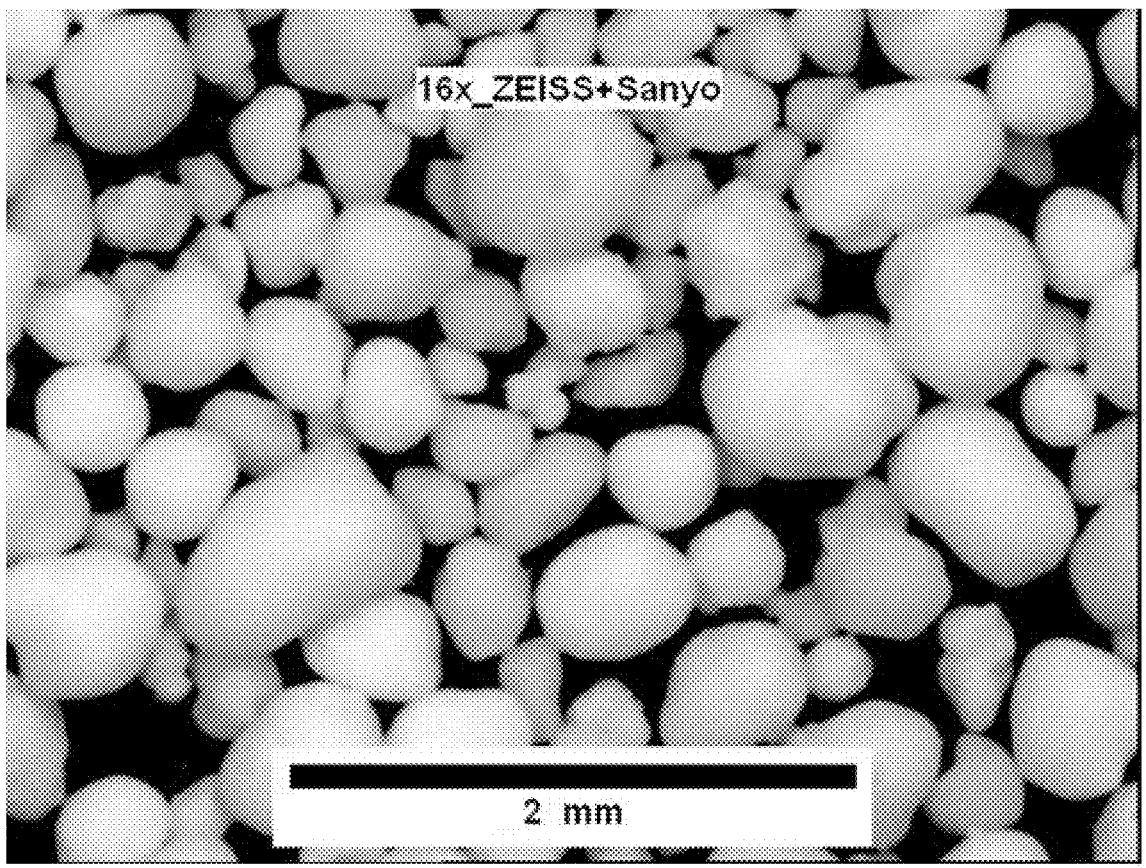
FIG. 2 is a microscopic photograph of salt particles according to the invention with a relative large average particle size, visibly larger than those of FIGS. 1(a) and (b) whereby the particles have a more or less rounded off structure.

The granulate material formed in said fluidized bed spray granulation process consists of agglomerated particles. These particles tend to have a blackberry like structure, in particular in the earlier stage of the agglomeration process when the size of the particles is still relative small, or have a more rounded off, when growing larger, likewise with more spherical like structure (see FIGS. 1, 1(b) and 2).

Figure 3:
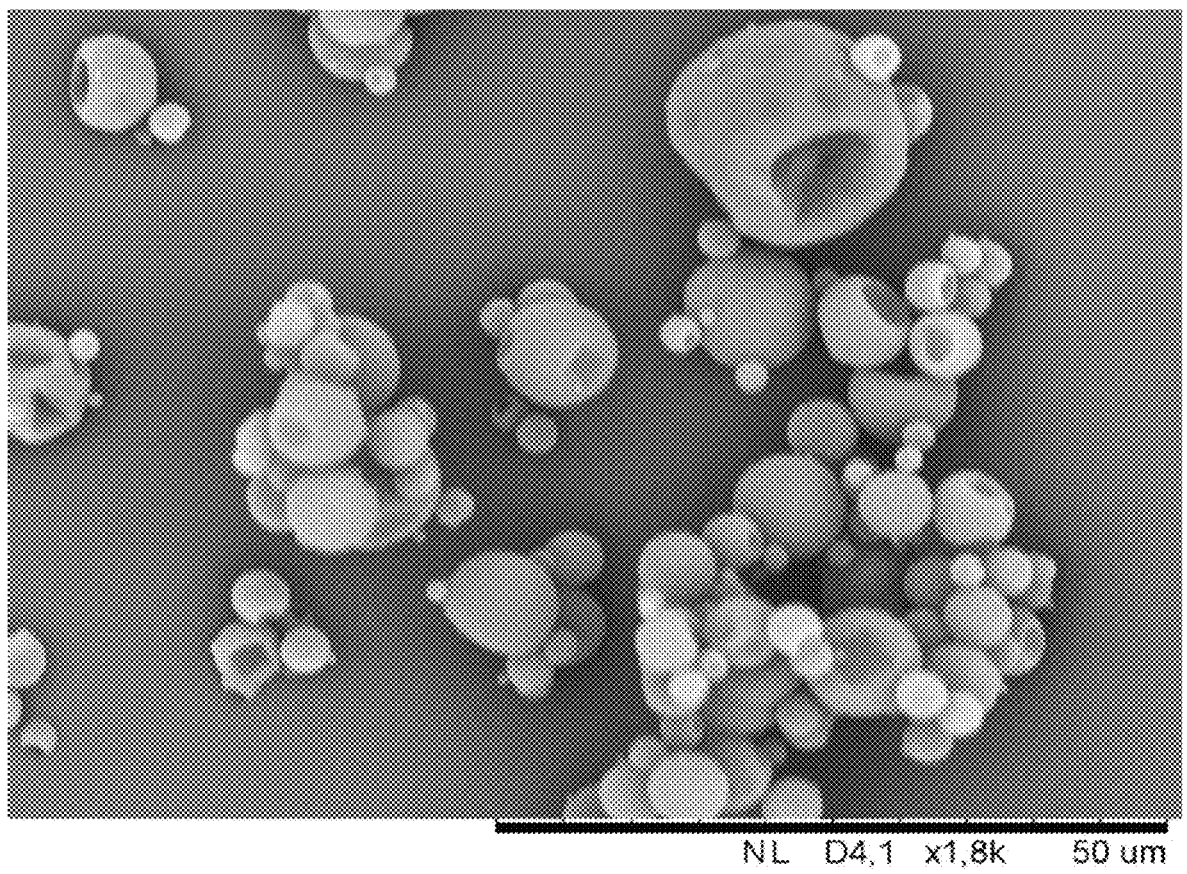
FIG. 3 is a microscopic photograph of a salt prepared by spray drying according to a comparative experiment whereby the salt particles have a kind of puffed open popcorn type of structure or little droplets that are burst open.
Figure 4:
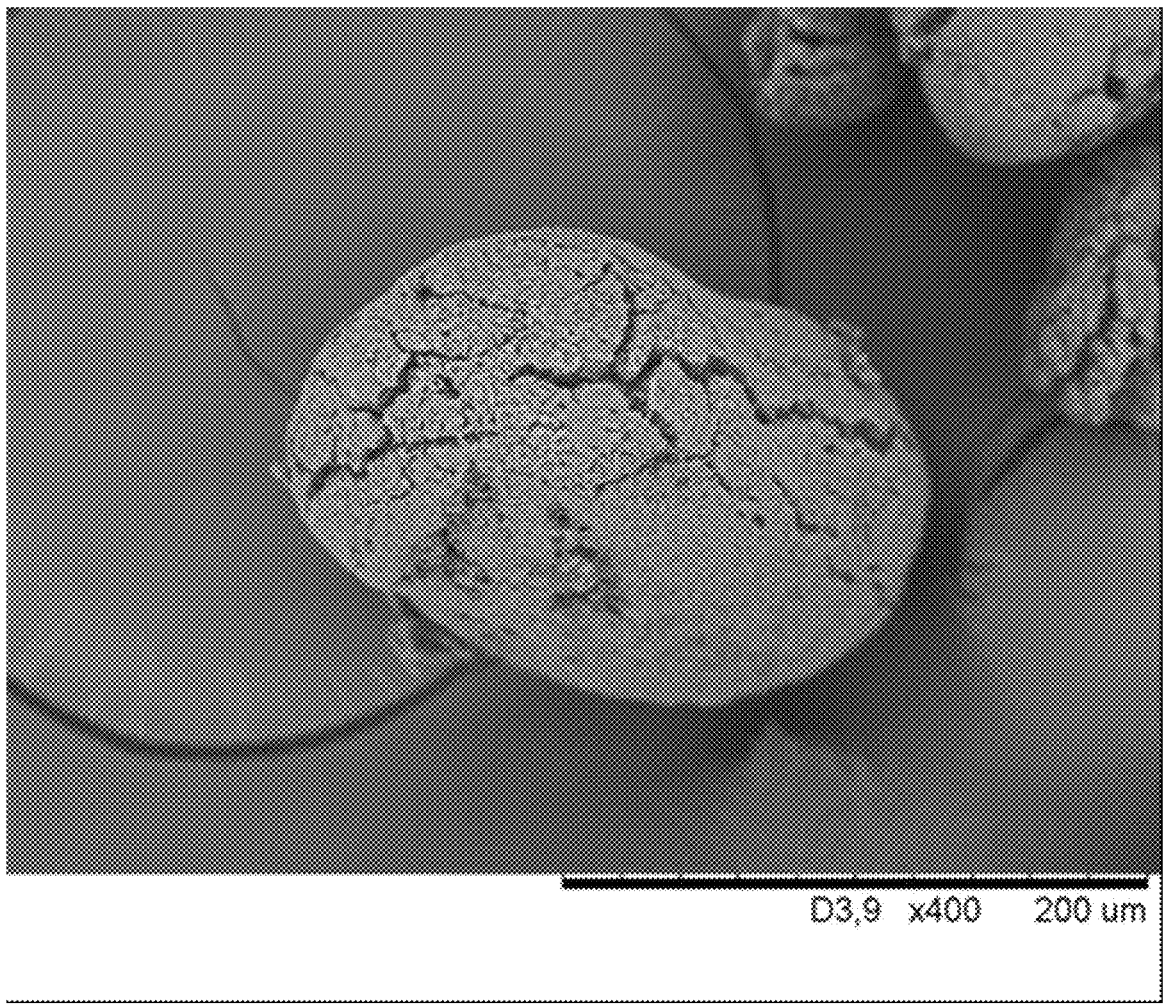
FIG. 4 is a microscopic photograph of a salt prepared by dosing liquid diamine to a solid dicarboxylic acid according to a comparative experiment whereby the salt particles have a potato shape with a cracked surface like dried mud with many sub-micron crystallites.

In contrast to the granulate salt material obtained by the process according to the invention, salt in particulate form obtained by spray drying typically has a kind of puffed open popcorn type of structure or little droplets that are burst open (see FIG. 3). Salt in particulate form obtained by a dry solid process comprising dosing diamine to solid dicarboxylic acid shows a potato shape with a cracked surface like dried mud with many sub-micron crystallites (see FIG. 4). Salts precipitated from aqueous solution generally show a (partially) crystalline, needle shape, or very fine powder, or when obtained by evaporation may show big lumps.

Suitably, the granulate salt material according to the invention has a particle size distribution with a median particle size (d50) in the range of 50-3000 μm, preferably in the range of 200-1000 μm, more preferably 400-750 μm. Herein the particle size distribution is measured with laser granulometry by the method according to ISO 13320-1 at 20° C.

The granulate salt material according to the invention has further interesting properties such as high density and low compressibility. The compressibility is determined by comparing the aerated bulk density (ABD) and the tapped bulk density (TBD). Each of the aerated bulk density (ABD) and the tapped bulk density (TPB) are measured by the method according to ASTM D6393. Suitably, the compressibility, expressed by the ratio of (TBD-ABD)/TBD*100%, is at most 25%.

Suitably, the granulate salt material has a tapped bulk density in the range of 350-750 kg/m$^3$; preferably the tapped bulk density is in the range of 450-700 kg/m$^3$. The advantage of a higher tapped bulk density is that a higher reactor loading can be applied in the DSSP process, resulting in a better capacity utilization.

The invention also relates to a process for preparing a nylon polymer. The process comprises direct solid state polymerization (DSSP) of a diammonium dicarboxylate salt (i.e. a nylon salt), wherein the salt is a granulate salt material prepared by fluidized bed spray granulation.

In such process, the salt is polymerized by applying a suitable heating profile, in which the temperature remains below the melting temperature of the salt. Preferably, during the direct solid state polymerization, the granular salt material is heated to elevated temperature, and wherein said temperature is kept below the melting temperature of the salt minus 10° C., preferably below the melting temperature of the salt minus 15° C.

According to one embodiment of the invention, the granulate diammonium dicarboxylate salt material obtained by fluidized bed spray granulation is used as such in the direct solid state polymerization. Herein is meant that the salt as obtained from the fluidized bed spray granulation, has not been subjected to a pelletizing step or any other shaping step, nor has been dissolved or dispersed in a liquid medium, before or during the direct solid state polymerization.

Suitably, during the direct solid state polymerization the granulate salt material and the resulting nylon polymer are mechanically agitated. Mechanical agitation may be accomplished, for example, by rotation or by stirring with an agitator, or a combination thereof. In a preferred embodiment, said DSSP process is carried out in a reactor comprising an agitator or in a rotatable reactor, e.g. tumble drier. The process has the advantages of limited attrition and limited scaling as described above.

The polyamide prepared by the DSSP process suitably is a copolyamide of one or more semi-aromatic polyamides and one or more aliphatic polyamides; or one or more aromatic polyamides and one or more aliphatic polyamides; or one or more semi-aromatic polyamides and one or more aromatic polyamides; and combinations thereof. Herein the constituting polyamide components are suitably selected from various aromatic polyamides, semi-aromatic polyamides and aliphatic polyamides and prepared from the corresponding salts comprising the corresponding mixed diamines and/dicarboxylic acids, as described herein above.

The invention also relates to a polyamide granulate material. The said granulate material comprises a polyamide polymer and is obtained by direct solid state polymerization of a diammonium dicarboxylate salt prepared by fluidized bed spray granulation process. The advantages thereof are that the said polyamide material is not only prepared in an efficient manner by DSSP, it also requires less extensive steps for cleaning and de-dusting and is more easily discharged than corresponding polyamides with the same composition obtained from salts prepared by other routes. Moreover, the polyamide granulate material is good flowing and easy to handle in further processing Herein the polyamide granulate material can be any polyamide granulate material obtained from any diammonium dicarboxylate salt as described above and obtained by the process according to the invention or any preferred or particular embodiment thereof as described above.

The polyamide granulate material according to the invention comprises an AABB polyamide, comprising alternating AA and BB repeating units, wherein AA represents the repeating units derived from diamine and BB represents the repeating units derived from dicarboxylic acid.

Next to the repeating units derived from diamine and repeating units derived from dicarboxylic acid, the polyamide may comprise some miner amounts of other repeating units, i.e. repeating units derived from other monomers. For example small amounts of monofunctional monomers and/or higher functional monomers may be included in the preparation of the salt and the polymerization thereof. Examples of such monomers are monofunctional amines, monofunctional carboxylic acids, triamines and trifunctional carboxylic acids. Suitably such other monomers are dissolved, next to the diamine and the dicarboxylic acid, in the aqueous medium used for the fluidized bed spray granulation. Preferably, the amount of such other monomers is low, for example below 5 mole %, more preferably below 2 mole %, and the polymer consists essentially of repeat units derived from diamines and dicarboxylic acids, i.e. for 95-100 mole %, preferably for 98-100 mole %. Herein the mole % is relative to the total molar amount of monomeric repeating units in the polyamide.

Examples of polyamides that can be prepared with the process according to the invention include the following semi-aromatic polyamides: PA-XT, PA-XI, PA-XT/XI, PA-XT/X6, XT/Y6 and PA-XT/YT, and any copolymer thereof, wherein T represents terephthalic acid, I represents isophthalic acid, 6 represents adipic acid, and X and Y represent diamines.

In a preferred embodiment, X and Y represent different diamines independently from each other chosen from aliphatic diamines from the group consisting of ethylene diamine, 1,4-diaminobutane, 1,5-diamine, 2-methyl-1,5-pentanediamine, 1,6-hexanediamine, 2,2,4-trimethyl-1,6-hexanediamine, 2,4,4-trimethyl-1,6-hexanediamine, cis-1,4-cyclohexanediamine, trans-1,4-cyclohexanediamine, 1,8-octanediamine, 1,9-nonanediamine, and 1,10-decanediamine, and any copolymer thereof.

Eventually the salt, and the polyamide prepared from the salt, may comprise three or more diamines. Suitably these diamines are selected in part, or even all, from the above group.

In a more preferred embodiment, the polyamides are derived from salts based on dicarboxylic acid consisting for at least 75 mole % of terephthalic acid, and diamine consisting for at least 75 mole % of 1,6-hexamethylenediamine (HMDA) and/or 1,4-diaminobutane (DAB) and/or 1,5-pentanediamine. Preferably the diamine comprises 1,6-hexamethylenediamine (HMDA) and 1,4-diaminobutane (DAB) in a molar ratio DAB/HMDA in the range of 25:75-45:55, or even better 30:70-40:60. Also preferable, the diamine comprises 1,6-hexamethylenediamine (HMDA) and 1,5-pentanediamine (PD) in a molar ratio PD/HMDA in the range of 30:70-70:30, or even better 40:60-60:40.

Even more preferred the dicarboxylic acid consists for 95-100 mole % of terephthalic acid, and the diamine consists for at least 95-100 mole % of 1,6-hexamethylenediamine (HMDA), 1,4-diaminobutane (DAB) or 1,5-pentanediamine. Suitably, the corresponding polyamides are either homopolymers PA-4T, PA 5T or PA6T, or copolymers thereof such as PA-4T/5T, PA-4T/6T and PA5T/6T, and PA4T/5T/6T.

Other examples of polyamides that can be prepared with the process according to the invention include the following aliphatic polyamides: PA-46, PA-66, PA-46/66, PA-66/68, and PA-410, and any copolymer thereof.

The polyamide may also be a copolyamide such as, for example, a copolyamide of one or more of the semi-aromatic polyamides and one or more of the aliphatic polyamides; one or more of the aromatic polyamides and one or more of the aliphatic polyamides; or one or more of the semi-aromatic polyamides and one or more of the aromatic polyamides; and combinations thereof.

Preferably the copolyamide is a copolyamide of one or more of the mentioned semi-aromatic polyamides and one or more of the said aliphatic polyamides. Examples thereof are PA-XT/YT/X6/Y6, wherein T represents terephthalic acid, 6 represents adipic acid, and X and Y represent different diamines. In these copolymers the diamine may also suitably comprise three or more diamines.

The granulate salt material according to the invention may also be used in a process wherein a diammonium dicarboxylate salt is polymerized in a liquid state. Herein the diammonium dicarboxylate salt suitably comprises a granulate salt material prepared by fluidized bed spray granulation and the granulate salt material is either molten or dissolved. For example, a 66 salt prepared by fluidized bed spray granulation can be advantageously used in a conventional melt polymerization process to produce polyamide-66, or a copolymer thereof. Another example is the polymerization of such a salt in a solution process in an aqueous solution to prepare a prepolymer, followed by isolation of the prepolymer and subsequent solid state post condensation to convert the prepolymer in a polyamide polymer.

EXAMPLES

The invention is further illustrated with the following examples and comparative experiments.

Materials

For the raw materials, terephthalic acid, adipic acid, 1,4-butanediamine, 1,5-pentanediamine and hexamethylenediamine, industrial grades were used.

Methods

Aerated Bulk Density (ABD) and Tapped Bulk Density (TBD)

The ABD and TBD were measured by the method according to ASTM D6393-08 ("Standard Test Method for Bulk Solids Characterization by Carr Indices", ASTM International, West Conshocken, PA, DOI: 10.1520/D6393-08) with a Hosokawa Powder Tester at 20° C.

Residual Water Content

The residual water content of a salt was determined by drying of the salt during 24 hours at 105° C. and under a vacuum of 100 mmHg, i.e. equal to an absolute pressure of 0.01 bar. The weight of the salt was measured before and after drying. The residual water content was calculated from the weight loss expressed as weight percentage relative to the weight of the granulate salt material before drying.

Compositions of Salts and Polymers

The composition of the salt with regard to ratio of diamines was determined by $^1$H-NMR determined by titration of a salt solution in water. The ratio of dicarboxylic acid/diamine was calculated form the excess of diamine determined by titration of a salt solution in water. The number of end groups, i.e. residual amine functional groups and residual carboxylic acid functional groups was determined by $^1$H-NMR.

Particle Size Distribution by Laser Diffraction

The particle size distribution of granulate material, and d10, d50 and d90 values, were measured by laser granulometry according to ISO 13320-1 with a Sympatec Helos (H0024) & Rodos apparatus at 20° C. with an applied pressure of 0.5 bar and an measured under-pressure in the venturi of 25 mbar. From the results the Span, defined by the ratio of (d90-d10)/d50, is calculated.

Flow Behavior in Shear Test

The flowability was measured by the method according to ASTM Standard D6773-08 ("Standard Shear Test Method for Bulk Solids Using the Schulze Ring Shear Tester", ASTM International, West Conshocken, PA, DOI: 10.1520/D6773-08). The shear test was performed with a Schulze Ringshear Tester at 20° C. with a consolidation stress of 3 kPa. The measurement was started immediately after filling of the tester. The flow behavior was performed on freshly prepared material, stored in a dry environment.

Experiments

Preparation of Salt Solution

For the preparation of salts by spray drying and spray granulation experiments, salts solutions were used, which were prepared as follows. A solution of terephthalic acid, 1,4-butanediamine and/or hexamethylenediamine in water were prepared by adding a 1,4-butanediamine solution in water, a hexamethylenediamine solution in water and terephthalic acid to a complementary amount of water under stirring and heating. The liquid mixture was heated to 60° C., upon which a clear solution was obtained. Upon cooling during storage, the dissolved salt partially crystallized out, resulting in a slurry. Upon reheating the partially crystallized salt dissolved again.

Solutions were prepared with concentrations between 28 and 50 wt. % salt. The concentration is calculated as the wt. % of all salt components, relative to the total weight of the solution. The applied ratio between 1,4-butanediamine and hexamethylenediamine was in the range of 36/64 and 42/58. The molar ratio between terephthalic acid and diamine was preset at 0.995, aiming at a slight excess of diamine.

Dry Salt Preparation

Dry salt preparation was carried out in a reactor equipped with a mechanical stirrer. Solid terephthalic acid (245 kg) was charged into the reactor, stirred and heated to 60° C. A mixture of 48 kg 1,4-butanediamine and 110 kg hexamethylenediamine was prepared in a dosing vessel and heated to 60° C. The diamine mixture was dosed to the terephthalic acid under stirring, while maintaining the temperature in the reactor between 30° C. and 95° C. After completion of the dosing the reactor content was kept at 95° C. while remaining stirring. The total batch cycle time of the salt formation step was 32 hours. Then the reactor content was cooled and discharged.

Two batches of terephthalic acid were used, one was an industrial grade used as received and the other one was a batch with smaller particle size obtained by sieving.

Properties of the salts prepared by this route, referred to as Dry-salt-1 and Dry salt-2 are shown in Table 1.

Spray Drying

Spray-drying was carried out in a spray dryer with an annular channel with a nitrogen loop and equipped with high pressure nozzles and a cyclone for separation of the fines. A 28 wt. % salt solution was heated to 50° C. and the gas inlet temperature was set at 160° C. The nozzle was pressurized to 55 bar. The product was obtained as a free flowing powder. Properties of the spray dried salt, referred to as SD salt, are shown in Table 1.

Fluidized Bed Spray Granulation

SG-1 and SG-2

Fluidized bed spray granulation was performed on pilot scale in a Glatt AGT 400 apparatus, comprising a spray column provided with spray nozzles at the top and center of the spray column and a classification channel at the center in the bottom. A salt solution was either freshly prepared or taken from storage and heated to 50° C.-60° C. The heating was performed by providing an electrical heating jacket around a storage bin. A fluidized bed of salt powder was prepared using a small amount of salt powder prepared on lab scale in a Glatt GPCC 3.1 apparatus. In the lab scale experiment, an initial bed was prepared from salt particles obtained by spray drying. The gas inlet temperature in the experiment on pilot scale was varied between 100° C. and 150° C. The flow of fluidization/heating gas was varied, thereby varying the residence time of the particles and allowing the particles to grow to larger particle size (SG-1) or smaller particle sized (SG-2). The bed temperature was controlled to be between 40° C. and 55° C. Properties of two examples of granulate salt materials (SG1 and SG2, with a monomer composition similar to in the comparative examples) obtained by the above fluidized bed spray granulation process are shown in Table 1.

SG-3

The procedure for SG-1 was repeated with a salt solution with a monomer composition based on terephthalic acid, 1,5-pentanediamine and 1,6-hexanediamine. The salt obtained had a residual water content of 5.2 wt. % and was dried afterwards to a residual water content of 2 wt. %. The properties of the granulate salt material SG-3 thus obtained are shown in Table 1.

SG-4

The procedure for SG-2 was repeated with a salt solution with a monomer composition based on terephthalic acid, adipic acid, 1,4-butanediamine and 1,6-hexanediamine. The salt obtained had a residual water content of 6.4 wt. % and was dried afterwards to a residual water content of 1.5 wt. %. The properties of the granulate salt material SG-4 thus obtained are shown in Table 1.

The reactor was charged with 300 gram of SD salt, i.e. the salt prepared by spray drying. The salt was stirred at a rotation speed of the stirrer of 30 rpm and inertized with nitrogen gas flow of 3 liter/hours at room temperature for 3 hours and then heated while kept under stirred motion, applying a temperature profile, wherein the salt was heated with a heating rate of 1° C./m in to 250° C., kept at that temperature for 16 hours. Then, the reactor content was cooled and discharged from the reactor. The following was observed: a lot of fines was formed; the flow behavior was extremely bad, prohibitive for a large scale experiment. The discharged material was collected and analyzed, the internal of the reactor showed hardly any fouling or scaling.

Other Experiments on Lab Scale

Comparative Experiment A was repeated with the salt materials Dry-salt-1 and Dry salt-2, and SG-1 and SG-2, which showed all better results than Comparative Experiment A in that less fines were produced and flow of the materials was much better. In case of the salts obtained by the dry-route slightly more fouling was observed. Since these runs were OK, experiments on larger scale could be performed.

Comparative Experiment B: Direct Solid State Polymerization of Dry-Salt-1

Direct solid state polymerization (DSSP) at larger scale was carried out in a 1 m3 reactor equipped with a mechanical stirrer. Prior to the experiment the reactor was cleaned and inertized with nitrogen gas. Then the reactor was charged with 325 kg of salt powder Dry-salt-1 prepared by dry route as described before. The salt was stirred at a rotation speed of the stirrer of 16.4 rpm and heated while kept under stirred motion, applying a temperature profile, wherein the salt was heated with a heating rate of 0.5° C./min to 180° C., kept at that temperature for 4 hours, then

TABLE 1

Analytical results of granulate salt materials obtained by spray drying, by dry salt preparation and by fluidized bed spray granulation

|  | SD-salt | Dry salt-1 | Dry salt-2 | SG1 | SG2 | SG3 | SG4 |
| --- | --- | --- | --- | --- | --- | --- | --- |
| DAB/HMDA ratio | 42/58 [a] | 36/64 [a] | 36/64 [a] | 39/61 [a] | 39/61 [a] | 29/71 [b] | 31/69 [a] |
| Acid/Diamine ratio | 0.995 | 0.996 | 0.995 | 0.997 | 0.996 | 0.998 | 0.990 |
| D10 (μm) | 25 | 7 | 5 | 352 | 134 | 222 | 83 |
| D50 (μm) | 89 | 190 | 79 | 560 | 301 | 359 | 243 |
| D90 (μm) | 198 | 900 | 377 | 739 | 467 | 527 | 372 |
| Span | 1.94 | 4.70 | 4.74 | 0.69 | 1.10 | 0.85 | 1.19 |
| Aerated Bulk density (kg/m$^3$) | 223 | 367 |  | 679 | 535 |  |  |
| Tapped Bulk density (kg/m$^3$) |  | 629 |  | 731 | 593 |  |  |
| Compressibility (%) |  | 42 |  | 7 | 10 |  |  |
| Residual water content (wt. %) | 1.6 | 1.8 | 1.8 | 3.7 | 0.7 | 5.2 (then dried to 2.0) | 6.4 (then dried to 1.5) |
| Flow behavior | Free flowing | Free flowing | Free flowing | Free flowing | Free flowing | Free flowing | Free flowing |

[a] DAB/HMDA ratio;
[b] PD/HMDA ratio.

Comparative Experiment A

A direct solid state polymerization (DSSP) was carried out in a 1 liter lab scale reactor equipped with a mechanical stirrer. During heating of the salt in the DSSP process, polymerization takes place, the salt is transformed and a polymer is formed. During the polymerization some diamine can be lost, resulting in some excess of dicarboxylic acid.

further heated with a heating rate of 10° C./min to 265° C. and kept at that temperature for 14 hours. During the polymerization some diamine might have been lost, resulting in some excess of dicarboxylic acid. Additional diamine was dosed to the reactor content at the end of the reported temperature profile and maintained at that temperature until a VN of 70-74 was obtained. The reactor content was cooled and discharged from the reactor. The discharged material was collected and analyzed, and the internal of the reactor was inspected for fouling and any other defects. 220 kg of polymer came out of the reactor (68 wt. % yield, max. theoretical yield is 87 wt. %), the rest of the material stayed behind as scaling and fouling of the reactor wall and internals.

Comparative Experiment C—Direct Solid State Polymerization of Dry-Salt-1

Comparative Experiment B was repeated except that Dry-salt-2 was used instead of Dry-salt-1. The yield was 65 wt. %, (max. theoretical yield is 87 wt. %), the rest of the material stayed behind as scaling and fouling of the reactor wall and internals.

Example I: Direct Solid State Polymerization of SG-1

Comparative Experiment B was repeated except that SG-1 was used instead of Dry-salt-1. The yield was 86 wt. %. The internal of the reactor showed hardly any fouling or scaling.

Example II: Direct Solid State Polymerization of SG-2

Comparative Experiment B was repeated except that SG-2 was used instead of Dry-salt-1. Also the amount of salt charged to the reactor was increased to 450 kg. The yield was 86 wt. %. the internal of the reactor showed hardly any fouling or scaling.

Properties and analytical results of the granulate polymer material obtained by DSSP for the Examples (EX 1-2) and Comparative Experiments (CE A-C) are shown in Table 2.

TABLE 2

Analytical results of polyamide products obtained by DSSP

| | CE-A | CE-B | CE-C | EX-I | EX-II |
|---|---|---|---|---|---|
| Salt | SD salt | Dry salt-1 | Dry salt-2 | SG1 | SG2 |
| Acid end groups (meq/kg) | 455 | 153 | 36 | 588 | 129 |
| Amine end groups (meq/kg) | <10 | 102 | 120 | <10 | 25 |
| Free acid (wt. %) | 1.04 | 0.50 | 0.45 | 0.48 | 0.03 |
| VN | n.m. | 85 | 69 | 71 | 75 |
| Tm | n.m. | 338 | 343 | 344 | 344 |
| D10 (μm) | n.m. | 20 | 8 | 314 | 136 |
| D50 (μm) | n.m. | 90 | 80 | 490 | 298 |
| D90 (μm) | n.m. | 330 | 173 | 693 | 464 |
| Span | n.m. | 3.44 | 2.06 | 0.77 | 1.10 |
| Bulk density (kg/m³) Aerated | n.m. | 435 | | 589 | 476 |
| Bulk density (kg/m³) Tapped | n.m. | 612 | | 663 | 606 |
| Compressibility (%) | n.m. | 29 | | 11 | 21 |
| Flow behavior | Very bad | Poor | Poor | Free flowing | Free flowing |
| Mass balance (%) | n.m. | 68 | 65 | 86 | 86 |

The results show that with the process according to the invention less fouling and agglomeration occurs. Moreover, the particle size distribution and the average particle size remains about the same, and also the Span factor remains about unaltered, indicative that a limited amount of fines is formed. Also the polymer material obtained with the process has retained free flowing properties.

The results for CE-B show a particle size distribution with a much smaller median particle size, and less large particles. Also a lot of scaling in the reactor was observed, which consisted of caked fine particles. Therefore, these fines are not measured in the remaining powder. These observations are indicative for the occurrence of extensive attrition, resulting of pulverization of the large particles in the salt into fines.

The results further show an excess of diamine end groups in the polymer of CE-C, in combination with a substantial amount of residual terephthalic acid. This illustrates that the post dosing was effective in compensating any loss in diamine, but not in reducing the amount of residual terephthalic acid. The polymer of EX-I shows a large excess dicarboxylic acid end groups, which is an indication that the post-dosing of diamine was incomplete. Nevertheless, the amount of residual terephthalic acid is not higher than in CE-B. The polymer of EX-II also shows an excess dicarboxylic acid end groups, but much smaller than for EX-I, which is an indication that the post-dosing of diamine was more complete for EX-II than for EX-I. Meanwhile, the amount of residual terephthalic acid for EX-II is much lower than for both EX-I and CE-B.

Example III: Direct Solid State Polymerization of SG-3

Comparative Experiment A was repeated except that SG-3 was used instead of the SD salt, and the amount of salt charged to the reactor was increased to 400 g. Furthermore, a modified temperature profile was applied: the temperature was raised to 220° C. with a heating rate of 1 C/min. Then the temperature was further increased to 240° C. with a heating rate of 2° C./hour, kept at 240° C. during 2 hours, heated to 250° C. in 1 hour and kept at that temperature during 4 hours. The product was obtained as a free flowing powder, the yield was 87 wt. % (compared to 91 wt. % theoretically) and the internal of the reactor showed hardly any fouling or scaling. The free acid content was 0.13 wt. %, acid end groups amounted to 221 meq/kg and amine end groups below 10 meq/kg. The bulk density aerated was 546 kg/m³ and the bulk density tapped was 630 kg/m³.

Example IV: Direct Solid State Polymerization of SG-4

Comparative Experiment A was repeated except that SG-4 was used instead of Dry-salt-1, the amount of salt charged to the reactor was increased to 400 kg, and the temperature profile was modified as follows: the temperature was raised to 210° C. with a heating rate of 1 C/min, and kept at that temperature for 15 hours. Then the temperature was further increased to 230° C. in 1 hour, and kept at 230° C. during 8 hours, heated to 240° C. in 1 hour and kept at that temperature for 14 hours. The product was obtained as a free flowing powder, the yield was 85 wt. % (compared to 86.8 wt. % theoretically). The internal of the reactor showed hardly any fouling or scaling. The content of free acid was 0.11 wt. %, acid end groups amounted to 245 meq/kg and amine end groups were about 19 meq/kg. The bulk density aerated was 489 kg/m³ and the bulk density tapped was 590 kg/m³.

These results of Examples III and IV show that the salts according to the invention a higher filler load can be applied compared to the SD material of Comparative Experiment A, while still obtaining a free flowing powder in a high yield, with a very low residual free acid content.

The invention claimed is:

1. A process for preparing a polyamide comprising conducting direct solid state polymerization (DSSP) of a diammonium dicarboxylate salt, wherein
   the diammonium dicarboxylate salt is a granulate salt material prepared by fluidized bed spray granulation of an aqueous solution or slurry comprising diammonium dicarboxylate salt dissolved or dispersed in an aqueous medium, and wherein
   the diammonium dicarboxylate salt has the following physical properties:
   (a) a particle size distribution with a median particle size (d50) in the range of 200-1000 μm, measured by laser granulometry with the method according to ISO 13320-1 at 20° C., and
   (b) a tapped bulk density in the range of 350-750 kg/m$^3$, measured by the method according to ASTM D6393.

2. The process according to claim 1, wherein the granulate salt material is a nylon salt.

3. The process according to claim 2, wherein the direct solid state polymerization (DSSP) is carried out in a reactor comprising an agitator, or in a rotatable reactor, or a combination thereof, and wherein during the polymerization the granulate salt material and the resulting nylon polymer are mechanically agitated.

4. The process according to claim 1, which further comprising dosing additional diamine at least during some part of the direct solid state polymerization or after the direct solid state polymerization.

5. The process according to claim 1, wherein the polyamide is:
   (i) an aromatic polyamide selected from PA-MXDT and PA-PXDT;
   (ii) a semi-aromatic polyamide selected from the group consisting of PA-XT, PA-XI, PA-XT/XI, PA-XT/X6, XT/Y6 and PA-XT/YT, and any copolymer thereof, wherein T represents terephthalic acid, I represents isophthalic acid, 6 represents adipic acid, and X and Y represent diamines, independently from each other chosen from aliphatic diamines from the group consisting of ethylene diamine, 1,3-propanediamine, 1,4-diaminobutane, 1,5-pentanediamine, 2-methyl-1,5-pentanediamine, 1,6-hexanediamine, 2,2,4-trimethyl-1,6-hexanediamine, 2,4,4-trimethyl-1,6-hexanediamine, cis-1,4-cyclohexanediamine, trans-1,4-cyclohexanediamine, 1,8-octanediamine, 1,9-nonanediamine, and 1,10-decanediamine;
   (iii) an aliphatic polyamide selected from the group consisting of PA-46, PA-66, PA-46/66, PA-66/68, and PA-410, and any copolymer thereof; or
   (iv) a copolyamide of one or more of the semi-aromatic polyamides and/or one or more of the aliphatic polyamides, and/or one or more of the aromatic polyamides.

6. A polyamide granulate material which is obtained by direct solid state polymerization (DSSP) of a diammonium dicarboxylate salt, wherein
   the diammonium dicarboxylate salt is a fluidized bed spray granulation product of an aqueous solution or an aqueous slurry comprising a diammonium dicarboxylate salt dissolved or dispersed in an aqueous medium, and wherein
   the diammonium dicarboxylate salt has the following physical properties:
   (a) a particle size distribution with a median particle size (d50) in the range of 200-1000 μm, measured by laser granulometry with the method according to ISO 13320-1 at 20° C., and
   (b) a tapped bulk density in the range of 350-750 kg/m$^3$, measured by the method according to ASTM D6393.

7. The polyamide granulate material according to claim 6, wherein the polyamide granulate material comprises a polyamide polymer consisting of:
   (i) an aromatic polyamide selected from PA-MXDT and PA-PXDT;
   (ii) a semi-aromatic polyamide selected from the group consisting of PA-XT, PA-XI, PA-XT/XI, PA-XT/X6, XT/Y6 and PA-XT/YT, and any copolymer thereof, wherein T represents terephthalic acid, I represents isophthalic acid, 6 represents adipic acid, and X and Y represent diamines, independently from each other chosen from aliphatic diamines from the group consisting of ethylene, 1,3-propanediamine, diamine, 1,4-diaminobutane, 1,5-pentanediamine, 2-methyl-1,5-pentanediamine, 1,6-hexanediamine, 2,2,4-trimethyl-1,6-hexanediamine, 2,4,4-trimethyl-1,6-hexanediamine, cis-1,4-cyclohexanediamine, trans-1,4-cyclohexanediamine, 1,8-octanediamine, 1,9-nonanediamine, and 1,10-decanediamine;
   (iii) an aliphatic polyamide selected from the group consisting of PA-46, PA-66, PA-46/66, PA-66/68, and PA-410, and any copolymer thereof; or
   (iv) a copolyamide of one or more of the semi-aromatic polyamides and/or one or more of the aliphatic polyamides, and/or one or more of the aromatic polyamides.

8. A process for preparing a polyamide comprising polymerizing a diammonium dicarboxylate salt in a liquid state, wherein
   the diammonium dicarboxylate salt comprises a granulate salt material prepared by fluidized bed spray granulation that is either molten or dissolved, and wherein
   the granulate salt material is the spray granulation product of an aqueous solution or slurry comprising diammonium dicarboxylate salt dissolved or dispersed in an aqueous medium, and wherein
   the granulate salt has the following physical properties:
   (a) a particle size distribution with a median particle size (d50) in the range of 200-1000 μm, measured by laser granulometry with the method according to ISO 13320-1 at 20° C., and
   (b) a tapped bulk density in the range of 350-750 kg/m$^3$, measured by the method according to ASTM D6393.

* * * * *